US006565883B2

(12) United States Patent
Ogorka et al.

(10) Patent No.: US 6,565,883 B2
(45) Date of Patent: May 20, 2003

(54) CONTROLLED RELEASE ORAL COMPOSITIONS COMPRISING RIVASTIGMINE

(75) Inventors: Jörg Ogorka, Steinen (DE); Oskar Kalb, Lörrach (DE); Rajen Shah, Pune (IN); Satish Chandra Khanna, Bottmingen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/118,183

(22) Filed: Apr. 8, 2002

(65) Prior Publication Data

US 2003/0039692 A1 Feb. 27, 2003

Related U.S. Application Data

(63) Continuation of application No. 09/818,690, filed on Mar. 27, 2001, which is a continuation of application No. PCT/EP99/07298, filed on Oct. 1, 1999.

(30) Foreign Application Priority Data

| Oct. 1, 1998 | (GB) | ............................................. | 9821298 |
| Oct. 1, 1998 | (GB) | ............................................. | 9821299 |
| Dec. 3, 1998 | (GB) | ............................................. | 9826654 |
| Dec. 16, 1998 | (GB) | ............................................. | 9827624 |
| Apr. 6, 1999 | (GB) | ............................................. | 9907822 |
| Apr. 6, 1999 | (GB) | ............................................. | 9907823 |

(51) Int. Cl.$^7$ ............................ A61K 9/14; A61K 9/22; A61K 9/36; A61K 9/28; A61K 9/16
(52) U.S. Cl. ...................... 424/474; 424/464; 424/469; 424/468; 424/471; 424/472; 424/488; 424/489; 424/490

(58) Field of Search .................................. 424/464, 465, 424/468, 469, 471, 472, 474, 488, 489, 490

(56) References Cited

U.S. PATENT DOCUMENTS

| RE34,990 E | * | 7/1995 | Khanna et al. | ............. 424/473 |
| 5,472,710 A | | 12/1995 | Klokkers-Bethke et al. | |
| 5,681,584 A | * | 10/1997 | Savastano et al. | .......... 424/473 |
| 5,962,535 A | * | 10/1999 | Miyamoto et al. | .......... 514/724 |
| 6,004,582 A | * | 12/1999 | Faour et al. | ................. 424/473 |
| 6,100,494 A | | 8/2000 | Clancy et al. | |

FOREIGN PATENT DOCUMENTS

| DE | 38 05744 A | | 9/1988 |
| DE | 39 22 167 A | | 1/1991 |
| EP | 0 558 913 A | | 9/1993 |
| GB | 2203040 A | * | 10/1988 |
| GB | 2203040 A | | 10/1988 |
| WO | WO 94 28882 A | | 12/1994 |
| WO | WO 99 34782 A | | 7/1999 |
| WO | 00/19985 | * | 4/2000 |
| WO | WO 00/19985 | | 4/2000 |
| WO | WO 01/28553 | | 4/2001 |
| WO | 01/28553 | * | 4/2001 |

OTHER PUBLICATIONS

Tse F.L.S. et al., Pharmaceutical Research, vol. 15, No. 10, pp. 1614–1620 (1998).

* cited by examiner

Primary Examiner—Thurman K. Page
Assistant Examiner—S. Tran
(74) Attorney, Agent, or Firm—Joseph J. Borovian

(57) ABSTRACT

Pharmaceutical composition capable of releasing a therapeutically effective dose of active agent, e.g., rivastigmine, in a time-controlled manner.

6 Claims, No Drawings

CONTROLLED RELEASE ORAL COMPOSITIONS COMPRISING RIVASTIGMINE

This is a continuation of application Ser. No. 09/818,690 filed Mar. 27, 2001, which is a continuation of International Application No. PCT/EP 99/07298, filed Oct. 1, 1999, the contents of which are incorporated herein by reference.

This invention relates to a controlled release oral pharmaceutical composition and more particularly to a unit dosage that upon administration releases an active agent in a time-controlled fashion.

Controlled release formulations may be formulated with following aspects in mind:

a) the time until the release of active agent (lag time or delay time)

b) the rate of release of active agent (fast or slow)

c) the duration of release of active agent (long or short)

Such aspects may be observed in standard in vitro dissolution tests, e.g., in water or if desired in body fluids, e.g., artificial gastric juices.

Little has been published on reliable time-controlled release formulations allowing a release at a pre-determined time of a single or repeated doses of active agents. There exists a need for such formulations which are commercially acceptable.

After extensive testing, we have now found that it is possible to produce a pharmaceutical composition capable of releasing at a specific time, i.e., with a time delay or lag time, a pharmaceutical active agent or active agent mixture, e.g., substantially independently of the concentration and type of ions present in the gastrointestinal environment, e.g., hydrogen ions and hydroxyl ions, i.e., independently of pH, phosphate ions, and also independently of enzymes, present into the surrounding body fluid.

The present invention provides in one aspect a pharmaceutical composition comprising a first component comprising a first active agent dose wherein on contact with water (or body fluid) 70 to 95% of said dose is released in water within 3 to 4 hours, and a second component comprising a second active agent dose, a water soluble osmosis inducing agent and a water swellable excipient, said second component having a water (or body fluid) permeable coating which, in use upon penetration by water, ruptures after a certain delay time, e.g., due to the swelling of the swellable excipient, and releases (at a predetermined time) the active agent (hereafter referred to additionally as pharmaceutical compositions of the present invention).

The present invention also provides a pharmaceutical composition comprising a first component comprising an active agent wherein 70 to 95% of said active agent in first component is released in water within 3 to 4 hours, and a second component comprising the active agent, a water soluble osmosis inducing agent and a swellable excipient in water, said second component having a coating which, upon penetration by the aqueous fluids, breaks after a certain period due to the swelling of the swellable excipient, and releases the active agent at a pre-determined time.

By "within 3 to 4" hours is meant that at the end of a period of 3 to 4 hours the specified dose of active agent, e.g., >80% or >85%, has been released.

The active agent may be a single active agent or may be a mixture. The active agent may be the same in the first and second doses or different in each dose. Preferably the active agent is the same.

In one embodiment, the coating for the second component is a film, e.g., semi-permeable membrane. The swellable excipient swells in presence of water or body fluid which penetrates through the coating and creates mechanical pressure within the second component thereby causing the coating to rupture or break and the system to open, e.g., like a lid of a box. Also, the swellable excipient may act as an osmotic agent drawing the water into the second component. The thickness of the coating is one of the parameters that controls the time delay, with more coating resulting in a longer time delay.

It will be appreciated that the term "rupture" preferably refers to breaching but it may also refer to any film system which rapidly (e.g. over 30 minutes or less) dissolves or disappears or changes its properties to permit egress of the active agent.

In another aspect there is provided a controlled release formulation, e.g., the second component, for releasing an active agent dose after a lag time wherein the active agent is released 6 to 12 hours, e.g., 8 hours, after ingestion.

The second component may be coated with two films. A first film is directly in contact with the second component and is preferably a semi-permeable membrane. The second film may be a semi-permeable (e.g., allowing the passage of e.g. water or active agent in one direction) or permeable. The films used in this embodiment may be, e.g., 2 to 5 times, thinner than the one used in a one-film embodiment. Such a composition may provide if desired longer delay times for the second component with a good release of the second dose of active agent. It further provides certain advantages as, e.g., reducing the amount of coating used.

By "first component" is meant a component capable of releasing immediately or in a controlled manner, e.g., sustained release, a first therapeutically effective dose of active agent when said first component is put in contact with water or body fluids.

By "second component" is meant a component capable of releasing immediately or in a controlled manner, e.g., sustained release, a second therapeutically effective dose of active agent when said second component is contacted to water or body fluids.

By "semi-permeable membrane" is meant a membrane suitable for the passage of the water (or body fluid) into an active agent containing core which is coated with said membrane and hinders egress of a dissolved active agent out of the core.

By "film", "film-coating" or "membrane" is meant, unless stated otherwise, a coating which is applied onto a core component, e.g., the first or second component.

By "delay time or lag time" is meant the duration of time between administration of the composition and the release of an effective dose of active agent from the first or second component.

A person skilled in art will appreciate that various plasma profiles may be obtained by varying, e.g.:

the composition of the first and/or second components, e.g., the nature and amount of excipients and/or active agent(s)

the delay time the type of semi-permeable and/or non semi permeable membrane the speed and nature of the active agent release onset (e.g. fast, slow, exponential, logarithmic, linear), which may depend on the rate of rupture of the membrane.

The composition according to the invention may be used for administrating a wide variety of active agents.

The composition according to the invention is suitable for example for water-soluble and also water-insoluble, solid, pharmaceutical active ingredients, which may be inorganic or in particular organic active substances, and are to be used in accordance with their indication as analgesics, antipyretics, antirheumatics, sedatives, hypnotic agents, anti-epileptics, depressants and stimulants, anaesthetics, neuroleptic analgesics, antihistamines, antihypertensive agents, anticoagulants, antithrombotic agents, psychopharmacological agents, psycholeptics, chemotherapeutic agents, e.g. antibiotics, sulphonamides, antituberculosis agents (tuberculostatic agents) or also chemotherapeutic agents against tropical infections, diuretics, spasmolytics, cardiovascular agents, e.g. sympathomimetics, antihypertensive agents, cardiac stimulants, e.g. cardiac glycosides and digitaloids, parenteral sugar therapeutics, analeptics acting on the central nervous system, geriatric agents, tonolytics (of striated muscles), anti-Parkinson agents, cytostatic agents, immunosuppressants, tonics and vitamins, according to B. Helwig (Moderne Arzneimittel), 1980.

As antibiotics, penicillin, tetracycline, chlorotetracycline, bacitracin, nystatin, streptomycin, neomycin, polymicin, gramicidin, oxytetracyclin, chloramphenicol, erythromycin, rifampicin, cefazolin, cefoxitin, cefsulodin, cefotiam and mefoxin may be used, and as chemo-therapeutic agents sulfamethazine, sulfamerazine, sulfamethizole and sulfisoxazole may be used, as solid active ingredients for the presentation according to the invention. In addition, e.g. as sedatives and hypnotic agents chloral hydrate, pentabarbital, phenobarnital, secobarbital, codeine and carbromal may be used, and as cardiac glycosides and digitaloids digitoxin and digoxin may be used, and as sympathomimetics epinephrine may be used as the solid active substance in water-soluble form or water-insoluble form.

In particular, antipyretics, analgesics and antirheumatics may be used as the solid active ingredient in the presentation according to the invention in suitable water-soluble form or water-insoluble form, for example propyphenazone, aminophenazone, aspirin (ASA), antipyrine, methyl nifenazine, melaminsulfone, sulfenazone, phenacetin, pentazocine, lactophenin, paracetamol, quinine, flufenamic acid, mefenamic acid, tolfenamic acid, meclofenamic acid, niflumic acid, clonixin or clonixidin, flunixin, ibuprofen, suprofen, ketoprofen, fenoprofen, pirprofen, diclofenac, ibufenac, procticic acid, naproxen, cicloprofen, tolmetin, clopirac, tiaprofenic acid, oxaprozin, fenclozic acid, fentiazac, clidanac, fenclonac, fenoprofen, flurbiprofen, carprofen, sulindac, cinmetacin, fenbuten, etodolac, butifufen.

Most advantageously, psychopharmacological agents may be used as the solid active ingredient in the presentation according to the invention, e.g. neuroleptics, antidepressants, thymoleptics, thymerethical drugs and tranquilisers in water-soluble form or water-insoluble form, such as thioridazine, imipramine, desimipramine, clomipramine, ketimipramine, opipramol, amitriptyline, nortriptyline, reserpine, aromazine, chlorpromazine, fluopromazine, methopromazine, trimeprazine, diethazine, promethazine, aminopromazine, mepazine, pipamazine and maprotiline.

In addition, antihypertensive agents, such as oxprenolol and meloprolol may be used as the solid active ingredient in the presentation.

In a preferred embodiment a composition according to the present invention is used for administering Rivastigmine (Exelon®) which is useful in the treatment of patients with mild to moderately severe dementia of the Alzheimer type, also known as Alzheimer's Disease.

Rivastigmine may be administered as the hydrogen tartrate (hta) in unit dosage form, e.g., an immediate release capsule, at a dose of from 0.5 mg to 6 mg twice a day.

Little has been published in detail on Rivastigmine's biopharmaceutical properties in humans. It is rapidly and completely absorbed. We have found that it is metabolised mainly through hydrolysis by esterases, e.g., acetyl and butyryl cholinesterase and has a plasma half life of 1 hour. It is subject to pre-systemic and systemic metabolism. We now have found that sustained release formulations of Rivastigmine may be produced with advantageous properties, e.g., better tolerability. Suitable test may be effected in fasted beagle dogs.

According to the present invention, Rivastigmine may be used in the form of the free base or a pharmaceutically acceptable salt thereof. Preferably the hydrogen tartrate (hta) is used. The composition of the invention allows, e.g., the manufacture of once a day pharmaceutical oral forms for patients who have to take more than one dose of an active agent per day, e.g., at specific times, so that their treatment is simplified. With such compositions tolerability may be improved, e.g., with Rivastigmine, and this may allow a higher starting dose and a reduced number of dose titration steps.

In a further aspect the invention relates to a pharmaceutical composition comprising rivastigmine adapted so that in use on oral administration a therapeutically effective dose of rivastigmine is released only after 6 hours (hereafter referred to additionally as pharmaceutical compositions of the present invention).

In a further aspect the invention relates to a pharmaceutical composition capable of releasing twice on administration a therapeutically effective dose of rivastigmine at different intervals upon oral administration (hereafter referred to additionally as pharmaceutical compositions of the present invention).

In preferred pharmaceutical composition of the invention, a first therapeutically effective dose of rivastigmine is released within 3 to 4 hours of ingestion and, subsequently, a second therapeutically effective dose of rivastigmine is released 6 to 12, preferably a to 10 hours, after ingestion.

The first component may be produced, e.g., by any conventional methods to provide the desired controlled release characteristics. It may be produced in solid form, e.g., a tablet, (e.g., a matrix-tablet), coated particles (e.g., non-pareilles) or pellets, e.g., coated pellets.

In one embodiment of said first component, the active agent is incorporated in a hydrophilic substance forming a gel substance on contact with water, e.g., which may be present in a ratio of from 10 to 50%, e.g., 15 to 45%, by weight of the first component, e.g., in the form of a controlled release tablet formulation, e.g., a matrix-tablet.

Hydrophilic gel forming substances commonly used in tablet formulations may be used and reference is made to the extensive literature on suitable substances, see in particular Fiedler's "Lexicon der Hilfstoffe", 4th Edition, ECV Aulendorf 1996 and "Handbook of Pharmaceutical Excipients" Wade and Weller Ed.(1994) the contents of which are incorporated herein by reference.

Preferred hydrophilic gel forming substances which may be used for the first component include one or more natural, partially or totally synthetic, anionic or, preferably, non-ionic hydrophilic gums, modified cellulose substances or protein aqueous substances such as, for example, acacia, gum tragacanth, locust bean gum, guar gum, karaya gum, agar, peptin, carrageen, soluble and insoluble alginates, methylcellulose, hydroxypropylmethylcellulose, hydroxypropylcellulose, hydroxyethylcellulose, sodium carboxymethylcellulose, carboxypolymethylene, gelatin. Preferred are cellulose which include methylcellulose, hydroxypropylcellulose and especially hydroxypropylmethylcellulose and sodium carboxymethylcellulose.

Especially preferred hydrophilic gel forming substances which may be used for the first component comprises high-viscosity hydrophilic swellable substances, e.g. substances having a viscosity in the range of 10,000 to 200,000 mPa-s, e.g. 50,000 to 150,000 mPa-s, e.g., 100,000 mPa-s. A preferred swellable substance which may be used is hydroxypropylmethylcellulose, e.g., Methocel, e.g., K100M (100,000 mPa-s/2% solution in water at 20° C.), having a methoxyl content of, e.g., 15 to 30%, e.g., 19 to 24%, and a hydroxypropoxyl content of, e.g., 5 to 15%, e.g., 7 to 12%. Swellable substances with diverse viscosities may be prepared as disclosed in "Handbook of Pharmaceutical Excipients" Wade and Weller Ed.(1994).

The weight portion of hydrophilic gel forming substances in the formulation may be from 10 to 50%, e.g., 25 to 50%, preferably 40%.

Said first component may comprise 3 to 20%, e.g. 5 to 15%, e.g. 6 to 13% by weight of the active agent, e.g., rivastigmine hydrogen tartrate (hta).

It may be also convenient to incorporate in the first component at least one of other soluble or insoluble pharmaceutical excipients as tablet diluents such as calcium sulphate, calcium phosphate, lactose, mannitol, sucrose. For example, microcristalline cellulose in granular powder and/or fine powder may be incorporated e.g. from 10 to 50%. For example, microcristalline cellulose fine powder may be present in a range of 20 to 50%, e.g, 30 to 40% by weight of the first component and microcellulose granular powder in a range of 10 to 40%, e.g., 20 to 30% by weight of the first component.

At least one glidant, e.g., dispersed silicon dioxide, talc, may be present in a range of 0.1 to 1% by weight of the first component and at least one tablet lubricant, e.g., magnesium sterate, steric acid, hydrogenated castor oil, polyetheylene glycol, may also be present in a range of 0.1 to 1% by weight of the first component, preferably 0.5%.

For example, the first component in this specific embodiment may have the following active agent, e.g., rivastigmine, release characteristic in water or artificial stomach juices (e.g. 0.1 N HCl):

| time (minutes) | amount (percentage) |
| --- | --- |
| 30 | 28–35 |
| 60 | 40–55 |
| 120 | 58–75 |
| 180 | 70–90 |
| 240 | 80–95 |
| 300 | 88–98 |
| 360 | >92 |

In a further embodiment of the first component, the active agent is incorporated in coated particles comprising a diffusion coating. The coating may be adapted to provide the controlled release of the active agent. Coating aids, conveniently used in coating formulation may be used. These coatings may include further binders, lubricants, glidants, stabilising agents, fillers or diluents, surfactants and the like. As disintegrants one can particularly mention CMC-Ca, CMC-Na, crosslinked PVP (Crospovidone, Polyplasdone of Kollidon XL), Alginic acid, sodium alginate and guar gum, most preferably crosslinked PVP, Crospovidine, crosslinked CMC and Ac-Di-Sol.

As binders which may be used in these coatings one can particularly mention polysaccharides, e.g. potato starch, wheat starch, corn starch, hydroxypropylmethylcellulose, e.g., products known under the registered trade marks Avicel®, Filtrac®, Heweten® or Pharmacel®.

Preferably cores which may be used for the first component are inert and water soluble. Typically the diameter is about 0.5 to 1.5 millimeters.

The coatings which may be used for the first component may comprise for example a cellulose derivative, e.g., which may be applied as a film. Common cellulose coatings may be used and reference is made to the extensive literature on suitable diffusion controlling substances.

As a preferred cellulose coating for the first component, one may use a coating comprising ethyl cellulose and hydroxypropyl methylcellulose (hereafter HPMC).

The ethyl cellulose has preferably a molecular weight 10,000 to 15,000,000, e.g., 50,000 to 1,000,000, e.g., 75,000 to 80,000, Daltons. It is preferably cellulose substituted by ca 2 to 3 ethoxy groups per unit saccharide. Preferably it has an ethoxy content of 44–51%.

Ethyl cellulose as used in the examples preferably is ethyl cellulose N10 Brand Aqualon® N10 (available from Dow Chemicals Company).

Hydroxypropyl methyl cellulose has preferably a viscosity of from 1 to 10 cps, e.g., 2 to 8 cps. Preferably it has a molecular weight of from 10,000 to 1,500,000 Daltons, e.g., 100,000 to 1,000,000, e.g., 300,000 to 800,000. It is preferably cellulose substituted by ethyl and hydroxypropyl groups.

Hydroxypropyl methyl cellulose preferably has a viscosity of 3 cps or 5 cps.

The particles may have a diffusion coating preferably comprising ethyl cellulose and hydroxypropyl methylcellulose, e.g., in a ratio of from 15:1 to 1:1, e.g., from 9:1 to 1:1, e.g., from 8:1 to 2:1, e.g., from 7:1 to 3:1.

The particles may have a drug (active agent) coating preferably comprising hydroxypropyl methylcellulose. The drug coating may contain about 50 to 90% by weight of said active agent, e.g., rivastigmine, for example from 50 to 80% by weight of rivastigmine. The amount of drug may comprise, e.g., 3–15% of the core.

Typically, the drug coating to diffusion coating ratio is from 3:1 to 1:1.

If desired a protective coating may be present between the diffusion coating and the drug coating. It may comprise hydroxypropylmethylcellulose or ethyl cellulose. The protective coating/diffusion coating ration may be, e.g., from 1:1 to 1:10, e.g., from 1:2 to 1:8.

Silica may be present, e.g, in 70% by weight of the film coating.

For example, the first component in this specific embodiment may have one or more, e.g., all of the following active agent, e.g., rivastigmine, release characteristic in water or artificial stomach juices (e.g. 0.1 N HCl):

| time (minutes) | amount (percentage) |
| --- | --- |
| 30 | 25–40 |
| 60 | 45–65 |
| 120 | 65–85 |
| 180 | 75–95 |
| 240 | 75–96 |
| 300 | 85–97 |
| 360 | 87–98 |
| 420 | 90–98 |
| 480 | 90–99 |

As a further example, the first component in this specific embodiment may have the following active agent, e.g., rivastigmine, release characteristic in water or artificial stomach juices (e.g. 0.1 N HCl):

| time (minutes) | amount (percentage) |
|---|---|
| 30 | 5–25 |
| 60 | 25–45 |
| 120 | 50–70 |
| 180 | 65–80 |
| 240 | 70–90 |
| 300 | 75–95 |
| 360 | 80–90 |
| 420 | 85–95 |
| 480 | 85–95 |

In a further embodiment of the first component, the active agent is incorporated into pellets, e.g. extruded pellets, which may be coated with a diffusion coating as previously described. The pellets may comprise the active agent, e.g., rivastigmine, in the same form as for the particles. It may further comprise binders as those mentioned above and diluents as calcium sulphate, calcium phosphate, lactose, mannitol or sucrose.

For example, the first component in this specific embodiment may have one or more, e.g., all of the following active agent, e.g., rivastigmine, release characteristics in water or artificial stomach juices (e.g. 0.1 N HCl):

| time (minutes) | amount (percentage) |
|---|---|
| 30 | 1–40 |
| 60 | 10–60 |
| 120 | 40–80 |
| 180 | 60–90 |
| 240 | 65–95 |
| 300 | 70–99 |
| 360 | 75–99 |
| 420 | >80 |

It may have preferably the following release characteristics:

| time (minutes) | amount (percentage) |
|---|---|
| 30 | 1–8 |
| 60 | 15–25 |
| 120 | 45–70 |
| 180 | 75–90 |
| 240 | 92–95 |
| 300 | 95–98 |
| 360 | 97–99 |
| 420 | >99 |

The present invention further relates to a controlled release oral pharmaceutical composition comprising a therapeutically effective dose of Rivastigmine and pharmaceutically acceptable excipients, e.g., the first component (hereafter referred to additionally as pharmaceutical compositions of the present invention).

The present invention further relates to a controlled release oral pharmaceutical composition comprising a therapeutically effective dose of Rivastigmine wherein in use 50 to 95%, e.g., 50 to 80%, 60 to 90%, 70 to 95%, of rivastigmine is released in water or body fluids, e.g., artificial stomach juices within 3 hours (hereafter referred to additionally as pharmaceutical compositions of the present invention).

The delay time for the second component may be determined precisely, e.g.,
- by the type and amount of water soluble excipients in the core
- by the water permeability and the number of film(s) coated on the second component
- by the mechanical strength, i.e., elasticity and tearing strength, of the film,
- by the type and amount of swellable excipient incorporated in the core.

An appropriate coating for the second component may be a semi-permeable membrane which is adapted to allow in use the passage of water (in use gastro-intestinal juices) into the core and to hinders egress of the dissolved active agent out of the core.

Water is drawn through the semi-permeable membrane at a rate which may be controlled by the composition of the membrane. The water which has penetrated the core dissolves at least part of the active agent. Osmotic pressure is thereby produced. The greater the pressure, the more molecules or ions go into solution, until under normal circumstances a saturated solution is produced.

In one embodiment, upon penetration by water or body fluid, the osmotic pressure, which as a consequence also induces swelling of the swellable excipient, may be produced by the active agent, e.g., rivastigmine, itself. However, a carrier which is soluble in water may be added in order to produce the necessary osmotic pressure. In this way, the osmotic pressure necessary for inducing the operating principle of the second component can be attained in such a way that the body fluid entering to balance the osmotic gradient produces the desired swelling of the swellable excipient (disintegrant) and after a certain delay time the rupturing or breaking of the film coating allows the release of the active agent. By optionally adding a water-soluble carrier in the core of the tablet, the second component may be produced in almost pH-independent form, i.e., independent of the concentration of hydrogen ions and hydroxyl ions and/or independent of other ions, such as phosphate ions, and also enzymes, for example in the alimentary tract.

Appropriate semi-permeable membranes for the film layer include the semi-permeable membranes described in literature, for example in U.S. Pat. Nos. 3,916,899 and 3,977,404, which are suitable for passage of the water (body fluid) and not the dissolved active agent and are thus suitable for bringing about osmosis. For example, artificially produced membranes may be used, which consist of cellulose acetate, cellulose triacetate, agar acetate, amylose acetate, cellulose acetate ethyl carbamate, cellulose acetate phthalate, cellulose acetate methyl carbamate, cellulose acetate succinate, cellulose acetate dimethylamino acetate, cellulose acetate ethyl carbonate, cellulose acetate chloroacetate, cellulose acetate ethyl oxalate, cellulose acetate methyl sulphonate, cellulose acetate butyl sulphonate, cellulose ether, cellulose acetate propionate, cellulose acetate diethylamino acetate, cellulose acetate octate, cellulose acetate laurate, methyl cellulose, cellulose acetate-p-toluenesulphonate, hydroxylated ethylene vinyl acetate, cellulose acetate butyrate and of other cellulose acetate derivatives. Other appropriate semi-permeable membranes are also hydroxypropylmethyl cellulose and polymeric epoxides, copolymers of alkylene oxide and alkyl glycidyl ether, polyglycols or polylactic acid derivatives and further derivatives thereof. In addition, mixtures may also be used, e.g. of water-insoluble acrylates, e.g., copolymer of ethyl acrylate and methyl methacrylate.

Generally, all semi-permeable membranes which are known from literature and have water-permeable properties are suitable for producing the film for the second component.

Coating of, e.g., tablets, e.g., compressed tablets, core particles or pellets, with a film comprising, e.g., a semi-permeable membrane of required thickness, may be effected in fluidised beds, coating pans or coating may be effected using, e.g., tabletting machines (dry coated tablet).

The second component may for example also be contained in a capsule, e.g., a gelatin capsule, which contains the active agent, e.g., rivastigmine, a swellable excipient, optionally a water-soluble carrier and other excipients, such as lubricants and sustained release agents in powder form, and is coated with the semi-permeable membrane as a film.

Appropriate films which may be used as a second coating for the second component include membranes which may be permeable or semi-permeable to water or body fluid, e.g., sustained release membranes, as described in literature. This second film-coating may be applied in the same manner as for the first film.

A preferred second film-coating for the second component comprises ethylcellulose, e.g. Ethylcellulose Brand Aqualon® N10 (available from Dow Chemicals Company). It may be applied, e.g., by spraying a solution comprising Ethylcellulose and HPMC 5 cps in a weight ratio of from e.g., 15:1 to 1:1, e.g., 9:1 to 1:1, e.g., from 8:1 to 2:1, e.g., from 7:1 to 3:1.

The ethyl cellulose has preferably a molecular weight 10,000 to 15,000,000, e.g., 50,000 to 1,000,000, e.g., 75,000 to 80,000, Daltons. It is preferably cellulose substituted by ca 2 to 3 ethoxy groups per unit saccharide. Preferably it has an ethoxy content of 44–51%.

Hydroxypropyl methyl cellulose has preferably a viscosity of from 1 to 10 cps, e.g., 2 to 8 cps, preferably 3 cps or 5 cps. Preferably it has a molecular weight of from 10,000 to 1,500,000 Daltons, e.g., 100,000 to 1,000,000, e.g., 300,000 to 800,000. It is preferably cellulose substituted by ethyl and hydroxypropyl groups.

In a preferred embodiment, the weight ratio between the first and the second film applied on the second component is 20:1 to 1:5, e.g., 15:1 to 1:1, e.g., 10.1 to 2:1.

In a preferred embodiment of the invention, the film thickness for the second component may be in a range of from 50 to 800 micrometers (em), e.g., 100 to 600 μM. For a second component having one film a preferred thickness is in the range of from 300 to 500 μm, e.g., 350 to 400 μm. For a second component having two films a preferred thickness is in the range of from 100 to 300 μm, e.g., 150 to 200 μm.

The nature and the amount of the excipients and the active agent of the second component (excluding film-coating(s) to be ruptured) may the same or not as the first component.

Suitable swellable excipients or disintegrating agents for the second component may be inert substances which swell rapidly upon contact with aqueous liquids, e.g., alginic acid and derivatives, agar-agar, cellulose such as microcrystalline or microfine cellulose, methyl cellulose, crosslinked carboxymethyl cellulose, carboxymethyl starch, modified starch, crosslinked polyvinyl polypyrrolidone, Colloidal silicon dioxide, high molecular weight polymers comprising ethylene oxide, bentonite, Veegum, montmorillonite, dried citrus pulp, xylans and also cationic and anionic exchangers such as cholestyramines.

Further excipients may be used to produce or induce the osmosis in the swelling process in the second component are water-soluble carriers (osmosis-inducing substances), e.g., substances that do not irritate the gastric or intestinal mucous membranes, e.g. inorganic or organic salts such as sodium chloride, sodium hydrogen phosphate, sodium nitrate and sodium acetate, or also acids such as tartaric, citric or also succinic acid and also sugars, especially e.g. mannitol, glucose, fructose, lactose and dextran compounds with different molecular weights. The amount of carrier may vary from a fragment to many times the quantity of rivastigmine employed.

The lubricants which may be an optional further excipient for the second component may be e.g., magnesium stearate, silicon aerogel, talc, stearic acid, hydrogenated castor oil, polyethylene glycol (PEG).

Optional additives for the second component may be, e.g., anti-oxidants, e.g, a-tocopherol or butylated hydroxytoluene (BHT).

Optional additives in film coating for the second component may be, e.g., pigments such as coloured iron oxides or titanium dioxide and/or flavourings, e.g., sweeteners, e.g., saccharine, Na cyclamate or sugar.

A preferred second component comprises, e.g., (weight%):

| Core | |
| --- | --- |
| Rivastigmine hta | 0.5 to 25% |
| Sodium Chloride | 10 to 35% |
| Avicel PH 102 | 5 to 25% |
| PVPP-XL | 20 to 70% |
| a-tocopherol | 0.01 to 5% |
| Aerosil 200 | 1 to 15% |
| Magnesium Stearate | 0.1 to 5% |
| First Coating: | |
| Cellulose Aceate | 1 to 20% |
| HPMC | 0.1 to 1% |
| Second Coating: | |
| Ethylcellulose | 0.5 to 10% |
| HPMC | 0.1 to 2% |

The invention further relates to a pharmaceutical composition comprising a core coated with two films, the first inner film being a semi-permeable to water or body fluids film applied directly on said core and comprising cellulose acetate, e.g., cellulose acetate E320 or 398-10, the second outer film being a permeable to water or body fluids film comprising ethylcellulose, e.g., Ethylcellulose N10.

The cores in question, comprising the active agent, e.g., rivastigmine, and excipients, e.g., may be the compressed tablets, capsules and pellets that are usual in galenics and may be produced by known processes. For example, the tablet mass may be produced by mixing the active agents disintegrant and optional further excipients, such as carriers, lubricants and if desired also sustained release excipients as required. Production of the compressed tablets and pellets may be effected, e.g., using the tabletting machines which are known for the preparation of for example round and rod-shaped compressed tablets and pellets, and the capsules are filled using known capsule filling machines.

The sustained release excipients that are used may be essentially water-insoluble excipients or mixtures thereof, e.g., lipids, inter alia fat alcohols, e.g. cetyl alcohol, stearyl alcohol and cetostearyl alcohol; glycerides, e.g. glycerin monostearate or mixtures of mono, di- and triglycerides of vegetable oils; hydrogenated oils, such as hydrogenated castor oil or hydrogenated cottonseed oil; waxes, e.g. beeswax or carnauba wax; solid hydrocarbons, e.g. paraffin or mineral wax; fatty acids, e.g. stearic acid; certain cellulose derivatives, e.g. ethyl cellulose or acetyl cellulose; polymers or copolymers, such as polyalkylenes, e.g. polyethylene, polyvinyl compounds, e.g. polyvinyl chloride or polyvinyl acetate, as well as vinyl chloride-vinyl acetate copolymers and copolymers with crotonic acid or polymers and copolymers of acrylates and methacrylates, e.g. copolymers of ethyl acrylate and methyl methacrylate.

A person skilled in the art may use other excipients than those disclosed above to obtain the desired effect. Reference is made to the extensive literature on suitable excipients provided in the art in particular Fiedler's "Lexicon der Hilfstoffe", 4th Edition, ECV Aulendorf 1996 and "Handbook of Pharmaceutical Excipients" Wade and Weller Ed. (1994) the contents of which are incorporated herein by reference.

As already stated initially, the release which is to be effected at different time intervals may be controlled precisely by the composition and the layer thickness of the coating (film) used for the second component, mechanical strength and elasticity and optionally through the quantity and swelling property of the swelling or disintegrating agent.

The second component, e.g., with one film, according to the invention may have one or more, e.g., all of the following release characteristics in water:

| time (minutes) | amount (percentage) |
|---|---|
| 0 | 0–1 |
| 120 | 0–1 |
| 180 | 0–1 |
| 240 | 0–85 |
| 300 | 0–97 |
| 360 | >99.5 |

The second component, e.g., with two films, according to the invention may have one or more, e.g., all of the following release characteristics in water:

| time (minutes) | amount (percentage) |
|---|---|
| 0 | 0–1 |
| 120 | 0–1 |
| 180 | 0–1 |
| 240 | 0–85 |
| 300 | 0–97 |
| 360 | 0–99.5 |
| 420 | 0–100 |
| 480 | 70–100 |
| 540 | 75–100 |
| 600 | 85–100 |
| 660 | 90–100 |
| 720 | >50 |

The rupture time may lead to 85% or more, e.g., 90%, of the active agent in the second component released within 30 minutes.

The pharmaceutical composition according to the invention preferably comprises from 0.5 to 25%, e.g., 1 to 10%, e.g., 2 to 5%, by weight of rivastigmine of the total composition.

The pharmaceutical compositions of the present invention are useful in the known indications of the particular active agent incorporated therein.

The exact amounts of active agent doses and of the formulation to be administered depend on a number of factors, e.g., the condition to be treated, the desired duration of treatment and the rate of release of active agent.

For example, the amount of the active agent required and the release rate thereof may be determined of the basis of known in vitro or in vivo techniques, determining how long a particular active agent concentration in the blood plasma remains at an acceptable level for a therapeutic effect.

For example, for rivastigmine, dosages in the range of 1 mg to 12 mg of active agent per day for a 70 or 75 kilogram mammal, e.g., humans, and in standard animal models, may be used. A surprisingly increased tolerability of rivastigmine provided by the compositions may be observed in standard animal tests and in clinical trials.

The pharmaceutical compositions of the invention are, e.g., administered, e.g., orally once-a-day, if two active agent doses are present and twice-a-day if a second active agent dose is present.

In a further aspect, the present invention provides the use of an active agent, e.g., rivastigmine, and excipients as defined above in the manufacture of a medicament for a once-a-day treatment of patients with, e.g., mild to moderately severe Dementia of the Alzheimer's type by oral administration.

In the following non-limitative examples, the invention is more fully clarified. If not otherwise stated, the parts are parts by weight. Temperatures are given in degrees Celsius.

Preparation of the First Component

The first component may be produced in conventional mariner by mixing the components. Below are examples of specific forms of first component allowing various release profile of the active agent contained therein.

EXAMPLE 1

First Component in the Form of a Matrix Tablet

The resultant mixture may be in powder form which may be pressed to form a tablet in conventional tabletting machines at compression pressures of, e.g., 2000 to 16000 lbs/sq.in.

A. Preparation of a Granulate

Ingredients rivastigmine, e.g., hta microcrystalline-cellulose, e.g., fine powder purified water for dissolving the drug substance Rivastigmine hta is dissolved in 10 to 20%, e.g., 16.3% by weight of purified water of the total granulate and the solution stirred until clear. A crossbar stirrer may be used at, e.g., 150–200 rpm, e.g., 180 rpm for 10–20 minutes, e.g., 15 minutes.

Microcrystalline-cellulose fine powder is sieved, e.g., through a manual or vibration sieve fitted with a screen and having a mesh width of, e.g., 1600 micrometers, and a wire diameter of, e.g., 500 micrometers, into a vessel of, e.g., a Collette Gral® 10 high shear mixer.

At mixer setting I and chopper setting I, the powder is wet granulated in the high shear mixer with the aqueous drug substance solution (granulation liquid) which is added at a rate of 0.5 to 1 l/min, e.g. 0.75 l/min.

The dissolving vessel (used for the preparation of the granulation liquid) is rinsed with the purified water and the rinsing liquid added at mixer setting I and chopper setting I at a rate of 0.5 to 1 l/min, e.g. 0.75 l/min.

The chopper setting is then increased to II and approximately 1 minute mixing is applied. The granulation stopped and the wall of the Collette Gral® vessel cleaned. The wet granulate is mixed for an additional minute at mixer setting I and chopper setting II.

The wet granulate is then dried by e.g. transferring it from the high shear mixer to a fluidized bed dryer bowl and applying an inlet air temperature from 40 to 60° C., e.g. 50° C., until a LOD (loss of density) of 2.5–5.0% is reached (corresponding to a product temperature of approx. 31° C.).

The dried granulate is then broken by e.g., passing it through an oscillator with a screen (e.g. mesh width 800 micrometers and wire diameter 320 micrometers) into the container of a free fall mixer (e.g. Turbula® T10A).

B. Preparation of the Tablet Mixture

Ingredients hydroxypropylmethyl-cellulose K100M
    microcrystalline cellulose, e.g., granular powder
    highly dispersed silicon dioxide

| Composition No. | 1 | 2 | 3 |
|---|---|---|---|
| rivastigmine hta (mg) | 7.2 | 7.2 | 7.2 |
| micocristalline cellulose fine powder (mg) | 25.95 | 25.95 | 25.95 |
| hydroxypropylmethylcellulose K100M (mg) | 18.75 | 22.50 | 30.05 |
| microcristalline cellulose granular powder (mg) | 22.35 | 18.60 | 11.05 |
| magnesium stearate (mg) | 0.375 | 0.375 | 0.375 |
| silicon dioxide highly dispersed (mg) | 0.375 | 0.375 | 0.375 |
| Total weight | 75 mg | 75 mg | 75 mg |

The compositions No. 1, 2 and 3 provide the following release profile when dissolved into water:

Composition 1:

| Time (min.) | 30 | 60 | 120 | 180 | 240 | 300 | 360 | 420 | 480 |
|---|---|---|---|---|---|---|---|---|---|
| Drug release (%) | 29.3 | 42.6 | 60.5 | 73.3 | 82.6 | 89.4 | 93.5 | 96.4 | 97.8 |

Composition 2:

| Time (min.) | 30 | 60 | 120 | 180 | 240 | 300 | 360 | 420 | 480 |
|---|---|---|---|---|---|---|---|---|---|
| Drug release (%) | 33 | 51.9 | 72.6 | 84.5 | 92.3 | 96.8 | 98.9 | 99.9 | 100 |

Composition 3:

| Time (min.) | 30 | 60 | 120 | 180 | 240 | 300 | 360 | 420 | 480 |
|---|---|---|---|---|---|---|---|---|---|
| Drug release (%) | 32.1 | 46 | 64.3 | 77.6 | 85.5 | 91.7 | 95.1 | 97.2 | 97.8 |

Microcrystalline-cellulose (MCC) granular powder, hydroxypropylmethyl-cellulose and silicon dioxide highly dispersed may be premixed manually in a plastic bag or in a free fall mixer for approximately two minutes. The silicon dioxide may be dispersed into the HPMC and MCC in order to reduce any dedusting during the subsequent sieving step.

The pre-mixture may be sieved by passing it through a sieve (or vibration sieve). The mesh width used may be, e.g., 800 micrometers and wire diameter 320 micrometers.

The dry pre-mixture may be transferred into the container of the free fall mixer (e.g. Turbula® T10A) and mixed with the granulate until 100 rotations are reached, e.g., 20 rpm for 5 minutes.

Magnesium stearate may be manually premixed with about 10 parts of the dry pre-mixture in plastic bag or in a free fall mixer for about two minutes. The magnesium stearate may be dispersed in order to prevent any re-agglomeration after the subsequent sieving step.

The premixture may be sieved by, e.g., passing it manually through a sieve (or vibration sieve). The mesh width used may be for example 800 micrometers and the wire diameter 320 micrometers.

The magnesium stearate pre-mixture is transferred into, e.g., the container of a free fall mixer (e.g. Turbula® T10A) containing the rest of pre-mixture and the whole tablet mixture is mixed until 100 rotations are reached, e.g., at 20 rpm for 5 minutes.

C. Tabletting

Tablets are formed by compression on, e.g., an excentic single punch tabletting machine (e.g. Comprex®) or a rotary tablet press (e.g., Betapress®, Korsch® PH250) using, e.g., 6 mm punches (round, convex, bevelled edges).

Non-limitative examples of the first component which may be prepared by the process disclosed above are provided in the following table:

EXAMPLE 2

First Component in the Form of Coated Particles

The preparation protocol of the film solutions is given hereafter. A non-limitative Example of a composition obtained according to this protocol will illustrate the invention.

A/ Ingredients

The ingredients for the preparation of the film solutions are provided in the following table:

| Component | Comment | Supplier |
|---|---|---|
| Rivastigmine hta | rivastigmine hydrogen tartrate | Novartis |
| Non-pareilles | sugar spheres 0.85–1.0 mm (USP) | H. G. Werner |
| HPM-cellulose 3 | Hydroxypropyl methylcellulose 3 cps | Shin-Etsu Chemicals Co. Ltd. |
| Ethylcellulose N10 | Ethylcellulose N10 | Dow Chemicals Company |
| HPM-cellulose 5 | Hydroxypropyl methylcellulose 5 cps | Dow Chemicals Company |
| Aerosil 200 | silicon dioxide highly dispersed | Degussa AG |
| Magnesium stearate | — | FACI SRL |
| Hardgelatine capsules | size 3, Cap + Body: rich yellow opaque, CONISNAP 6 dimple | Capsulgel N.V. |

B/ Preparation of Film Solutions

The % are expressed by weight of the solution prepared (qsp. purified water for 1, 2 and 3).

1. Preparation of the Aqueous HPMC-solution (5%)

HPMC 3 cps is dispersed in purified water in a stainless steel vessel while stirring approximately 2 min at 500 rpm in a crossbar stirrer. The solution is stirred until clear (30 min) at a speed of 250 rpm. The obtained solution is allowed to stand still for 12 h in a stainless steel vessel.

2. Preparation of the Aqueous Rivastigmine/HPMC Film Solution

Rivastigmine hta (15–25%) is dissolved in the HPMC-solution (3–5%) while stirring (Rivastigmine/HPMC solution). The solution obtained is stirred until clear (approx. 15 min) in a stainless steel vessel (crossbar stirrer speed: 250 rpm). Then, silicon dioxide (1–3%) is dispersed in the Rivastigmine/HPMC-solution while stirring in a stainless steel vessel (crossbar stirrer speed: 250 rpm). The solution obtained is stirred for approximately 10 minutes. If needed the silicon dioxide may be dispersed in 2 parts of the Rivastigmine/HPMC-solution using a mortar and pestle before adding the rest of the solution.

3. Preparation of the Aqueous HPMC Film Solution

Silicon dioxide (1.5–3%) is dispersed in the HPMC-solution 3 cps (3–7%) while stirring in a stainless steel vessel (crossbar stirred speed: 250 rpm). The solution is stirred for approximately 10 minutes. If needed, the silicon dioxide is dispersed in 2 parts of the Rivastigmine/HPMC-solution using a mortar and pestle before adding the rest of the solution.

4. Preparation of the Organic Solvent

Ethanol 94% (w/w) and acetone are mixed (see proportions in paragraph 5) during approximately 2 minutes in a stainless steel vessel acetone (crossbar stirrer speed: 250 rpm).

5. Preparation of the Organic Polymer Film Solution

Ethylcellulose N10 (5–10%) and the HPMC 5 cps (0.5–2%) are dispersed in a stainless steel vessel in the organic solvent (acetone (45–65%) and ethanol 94% (35–45%)) while stirring approximately 1 minute in a crossbar stirrer speed: 500 rpm stir the solution until clear approximately 30 minutes (speed: 250 rpm) in stainless steel vessel. The solution is let stand still for 12 hr.

C/ Coating

1. Aqueous Coating

A fluidized bed dryer Glatt WST 5 (batch size: approximately 1.5 kg) is adjusted to the required inlet air temperature (60° C.) and the spray rate to 15 g/min (pressure: 2.5 bar) by means of the variation of the peristaltic pump with a silicon tube (internal diameter 4.0 mm). The Wurster column (6 inch) with a binary spray nozzle (1.0–1.2 mm diameter) in the center of the base plate that sprays in line with the air stream, is pre-warmed to 45° C. The non-pareilles are added and the air flap is adjusted to the airflow required for gentle fluidization of the non-pareilles inlet air quantity approximately 325 m$^3$/h.). The Rivastigmine/HPMC-solution from step A is then sprayed immediately in order to minimise abrasion of the no stainless steel vessel non-pareilles. The product temperature is approximately 45° C.

Then, the stainless steel vessel and the silicon tubing are rinsed with the HPMC-solution 3 cps (approximately 25 g). For the protective coating, the aqueous HPMC-solution is sprayed (rinsing liquid—first; the rest of the HPMC-solution—second). The stainless steel vessel and the silicon tubing are then rinsed with purified water (approximately 25 g) and then the rinsing water sprayed.

2. Organic Coating

A fluidized bed dryer Glatt WST 5 (batch size: approximately 1.5 kg) is adjusted at the inlet air temperature (50° C.) and the spray rate to 25 g/min (pressure: 2.5 bar) by means of the variation of the peristaltic pump with silicone tube (internal diameter 4.0 mm). The Wurster column (6 inch) with a binary spray nozzle (1.0–1.2 mm diameter) in the center of the base plate that sprays in line with the air stream is used. The organic solvent is sprayed to remove the rest of the purified water from the tubing system and the nozzles (to prevent crystallisation of ethylcellulose (organic polymer film solution) in the tubes). The product temperature is approximately 40° C.

Then, the organic polymer film solution is sprayed. The stainless steel vessel and the silicon tubing are rinsed with approximately 50 g of the organic solvent ethanol/acetone and the rinsing liquid is sprayed. The coated non-pareilles are dried at an inlet air temperature of 50° C. until the product temperature increases by 2° C.

The coated non-pareilles are dried manually in a Waldner tray dryer (inlet air temperature: 30° C.) for 6 hours to remove any residue of the organic solvent from the coating and passed through a sieve (sieve size 1250 mm and wire diameter 400 mm) to remove agglomerates.

3. Preparation of the Capsule Filing Mixture

Magnesium stearate is manually passed through a sieve having a mesh width of 800 mm and a wire diameter of 320 mm. The sieved magnesium stearate is then mixed with the coated pellets in a free fall mixer (Turbula 10I) at 20 rpm for 5 minutes, i.e., 100 rotations.

4. Capsule Filing

The capsule filling mixture is filled on a automatic capsule filling machine (Zanasi LZ 5) into empty hardgelatine capsule shells (CONI-SNAP 6 dimple, size 3). The nominal fill weight is as mentioned above.

The process parameters are as follows:

speed: 3000 HK/h dosator/piston:

size: # 4 height: 12–14 mm vacuum: 0.7 bar feed hopper: none

D/ Preparation of a Composition of Exelon MR BID 4.5 Mg HKP

The composition is prepared according to the process described above. The ingredients are given in the table below:

| Phase | Components | weight (mg) | weight (mg) |
|---|---|---|---|
| aqueous drug substance/polymer solution [1,3] (drug loading) | rivastigmine hta | 7.20 | 7.20 |
| | hydroxypropyl methylcellulose 3 cps | 1.50 | 1.50 |
| | silicon dioxide highly dispersed | 0.75 | 0.75 |
| | purified water | 28.50 | 28.50 |
| aqueous polymer solution [1,3] (protective coating) | hydroxypropyl methylcellulose 3 cps | 1.50 | 1.50 |
| | silicon dioxide highly dispersed | 0.75 | 0.75 |
| | purified water | 28.50 | 28.50 |
| organic polymer solution [2,3] (diffusion coating) | ethylcellulose N10 | 4.05 | 7.35 |
| | hydroxypropyl methylcellulose 5 cps | 0.45 | 3.15 |
| | ethanol 94% (w/w) | 16.20 | 37.80 |
| | acetone | 24.30 | 56.70 |

[1] 5% HPMC-solution
[2] 10% polymer-solution/organic solvent (60% acetone, 40% ethanol 94% (w/w))
[3] 5% excess (loss on spraying)

| Composition of a capsule of Exelon MR BID 4.5 mg HKP | | | |
|---|---|---|---|
| Total film quantity (% of the theoretical capsule content (= 150 mg)) | | 3.0 | |
| Diffusion coating (ethylcellulose:hydroxypropyl methylcellulose) | | 90:10 | 70:30 |
| Phase | Component | i) | ii) |
| Core | non-pareilles (placebo) | 134.40 | 129.15 |
| Coating 1 | rivastigmine hta | 7.20 | 7.20 |
| (drug loading) | hydroxypropyl methylcellulose 3 cps | 1.50 | 1.50 |
| | silicon dioxide highly dispersed | 0.75 | 0.75 |
| Coating 2 | hydroxypropyl methylcellulose 3 cps | 1.50 | 1.50 |
| (protective coating) | silicon dioxide highly dispersed | 0.75 | 0.75 |
| Coating 3 | ethylcellulose N10 | 4.05 | 7.35 |
| (diffusion coating) | hydroxypropyl methylcellulose 5 cps | 0.45 | 3.15 |
| lubricant | magnesium stearate | 0.15 | 0.15 |
| Total fill weight | | 150.75 | 151.50 |
| capsules | CONISNAP size 3 | 49.00 | 49.00 |
| TOTAL (mg) | | 199.5 | 200.50 |

The following release profile is obtained

| Time (min.) Drug release (% in 0.1 HCl) | 30 | 60 | 120 | 180 | 240 | 300 | 360 | 420 | 480 |
|---|---|---|---|---|---|---|---|---|---|
| i) | 32.5 | 55.1 | 76.4 | 84.1 | 88.0 | 90.6 | 92.4 | 93.8 | 94.9 |
| ii) | 15.5 | 36.3 | 61.2 | 72.9 | 79.7 | 83.4 | 86.5 | 89.1 | 90.6 |

E/ Dosage Strengths

For all dosage strengths the same coated non-pareilles (with the same drug load) are used. Different dosage strengths (1.5 mg–9 mg) are obtained by varying the capsule fill weight, as outlined in the table below.

| Dosage strengths | capsule fill weight (approx.) | capsule size |
|---|---|---|
| 1.5 mg | 50 mg | 4 |
| 3.0 mg | 100 mg | 3 |
| 4.5 mg | 150 mg | 3 |
| 6.0 mg | 200 mg | 2 |
| 9.0 mg | 300 mg | 2 |

For the dosage strengths 6.0 mg, 3.0 mg and 1.5 mg, placebo non-pareilles could be added to optimise the filling degree of the capsules if needed.

EXAMPLE 3

First Component in the Form of Coated Pellets

A/ Ingredients

Rivastigmine hydrogen tartrate
Microcristalline cellulose Avicel® PH-101 (FMC Corporation, Philadelphia, USA)
Lactose 200 mesh (DMV, Vehgel, Netherlands)
Ethylcellulose N10 (Dow Chemicals Company, USA)
Hydroxypropyl methylcellulose 5 cps (Dow Chemicals Company, USA)
Magnesium stearate
Hardgelatine capsules: size 3, Cap+Body: rich yellow opaque, CONISNAP® 6 dimple (Capsulgel N.V.).

The amounts of the ingredients to be used are provided in the protocol description or in paragraph G/ below.

B/ Preparation of the Drug and Film Solutions

The % mentioned below in 1, 2 and 3 are expressed by weight of the solution prepared:

1. Preparation of the Aqueous Rivastigmine Solution

Rivastigmine is dissolved in water, e.g., in a stainless steel vessel, while stirring and the solution is stirred until clear approximately 15 min at 250 rpm in, e.g., a crossbar stirrer. The amount of water is about 39% of the dry core weight which are prepared as described below.

2. Preparation of the Organic Solvent

Ethanol 94% (w/w) and acetone are mixed (acetone (60%)/ethanol 94%(40%)) during approximately 2 minutes in a stainless steel vessel (crossbar stirrer speed: 250 rpm).

3. Preparation of the Organic Polymer Film Solution

Ethylcellulose N10 (8%) and the HPMC 5 cps (2%) are dispersed in a stainless steel vessel in the organic solvent (90%) while stirring approximately 1 minute in a crossbar stirrer (speed: 500 rpm). The solution is stirred until clear approximately 30 minutes (speed: 250 rpm) in, e.g., stainless steel vessel. The solution is allowed to stand for 12 h.

Preparation of the Pellets

The lactose and Avicel® are loaded in a Collette Gral® (10 or 25 L) and mixed for 2 minutes (plow-slow, Chopper-slow). The rivastigmine solution is added into the mix of Avicel® and lactose in the Collette Gral® with the plow at slow speed (Chopper-off).

After the drug solution is pumped into the Collette Gral®, additional water is added to the same container for rinsing. The quantity of the additional water is 18.5% of the dry weight of the core. This additional water is pumped into the mix from above with plow at slow speed(Chopper-off).

The mix from above is granulated in the Collette Gral® for about 15 minutes (Plow slow, Chopper-off). The machine is stopped at 5 minute intervals and the walls of the vessel scraped. The chopper is turned on at slow speed for the last two to three minutes. The wet mass from above is extruded into thin strands (Parameters: Twin screw extruder from Gabler®, screen size: 1 mm, screw speed: 50 rpm, dosage machine position: 1.8, pressure of the mass: 10 bar).

The extruded mass is spheronized, i.e., formed into pellets, using a 3 kg charge at a time (Parameters: Spheronizer from Wyss Pharmex®, charge in the spheronizer: 3 kg, rotational speed: 870 rpm, spheronization time: 6 minutes).

The wet pellets are dried (Parameters: Aeromatic® fluid bed drier, inlet air temperature: 60° C., exhaust temperature: 47 to 49° C., dry to LOD (loss of drying) of 2.5 to 3.0%).

The dried pellets are manually sieved to exclude the agglomerates. All that passes through the sieve is collected for coating (sieve size:1600 micrometers).

D/ Coating

1. Organic Coating

A fluidized bed dryer Glatt® WST 5 (batch size: approximately 1.5 kg) is adjusted at the inlet air temperature (50° C.-325 m³/h) and the spray rate to 25 g/min (pressure: 2.5 bar) by means of the variation of the peristaltic pump with silicone tube (internal diameter 4.0 mm). The Wurster column (6 inch) with a binary spray nozzle (1.0–1.2 mm diameter) in the center of the base plate that sprays in line with the air stream is used. The organic solvent is sprayed to remove the rest of the purified water from the tubing system and the nozzles (to prevent crystallisation of ethylcellulose (organic polymer film solution) in the tubes). The product temperature is approximately 40° C.

Then, the organic polymer film solution is sprayed. The stainless steel vessel and the silicon tubing are rinsed with approximately 50 g. of the organic solvent ethanovacetone and the rinsing liquid is sprayed. The coated pellets are post-dried at an inlet air temperature of 50° C. until the product temperature increases by 2° C.

The coated pellets are dried manually in a Waldner® tray dryer of type HW 15/2N (inlet air temperature: 30° C.) for 6 hours to remove any residue of the organic solvent from the coating and then passed through a sieve (sieve size 1600 micrometers and wire diameter 400 micrometers) to remove agglomerates.

E/ Preparation of the Capsule Filing Mixture

Magnesium stearate is passed through a sieve having a mesh width of 800 micrometers and a wire diameter of 320 micrometers. The sieved magnesium stearate is then mixed with the coated pellets in a free fall mixer (Turbula® 10I) at 20 rpm for 5 minutes, i.e., 100 rotations.

F/ Capsule Filing

The capsule filling mixture is filled on a automatic capsule filling machine (Zanasi® LZ 5) into empty hardgelatine capsule shells (CONI-SNAP® 6 dimple, size 3). The nominal fill weight is as mentioned above (Process parameters: speed: 3000 HK/h, dosator/piston: size #4 and height: 12–14 mm, vacuum: 0.7 bar, feed hopper: none).

G/ Composition of Exelon MR BID 4.5 Mg HKP

The composition is prepared according to the process described above.

| Total film quantity (% of the theoretical capsule content (= 150 mg)) | | 3.0 |
|---|---|---|
| Diffusion coating (ethylcellulose:hydroxypropyl methylcellulose) | | 80:20 |
| Phase | Component | weight (mg) |
| Core | rivastigmine hta | 7.20 |
| | lactose 200 mesh | 60.30 |
| | microcrystalline cellulose (Avicel ®) | 67.5 |

-continued

| Diffusion coating | ethylcellulose N10 | 3.24 |
|---|---|---|
| | hydroxypropyl methylcellulose 5 cps | 0.81 |
| lubricant | magnesium stearate | 0.15 |
| Total fill weight | | 139.20 |
| capsules | CONISNAP ® size 3 | 49.00 |
| TOTAL | | 188.20 |

The following release profile is obtained:

| Time (min.) | 30 | 60 | 120 | 180 | 240 | 300 | 360 | 420 |
|---|---|---|---|---|---|---|---|---|
| Drug release (% in 0.1N HCl) | 4.2 | 21.9 | 57.8 | 84.8 | 94.5 | 97.9 | 99.4 | 99.9 |

H/ Dosage Strengths

For all dosage strengths the same pellets (with the same drug load) are used. Different dosage strengths (1.5 mg–9 mg) are obtained by varying the capsule fill weight, as outlined in the table below.

| Dosage strengths | capsule fill weight (approx.) | capsule size |
|---|---|---|
| 1.5 mg | 46.4 mg | 4 |
| 3.0 mg | 92.8 mg | 3 |
| 4.5 mg | 139.2 mg | 3 |
| 6.0 mg | 185.6 mg | 2 |
| 9.0 mg | 278.4 mg | 2 |

For the dosage strengths 6.0 mg, 3.0 mg and 1.5 mg, placebo pellets could be added to optimise the degree of filling of the capsules if needed.

Preparation of the Second Component

The second component may be produced in conventional manner by mixing the components, e.g., in order to obtain coated particles or pellets as for the first component and then by applying one or more film coatings as above described.

EXAMPLE 4

Second Component in the Form of a Matrix Tablet Coated with One Film

A second component which contains 4.8 mg rivastigmine hta as the rivastigmine in the pressed core, e.g. compressed tablet, is coated with an appropriate film. This system, that releases the rivastigmine after a pre-determined time when placed in an aqueous fluid, may be produced as follows:

A. Preparation of the Core

The mass for 5000 cores is prepared as follows. 24 g of rivastigmine hta are dissolved in 1000 g of purified water. 400 g of Polyplasdone (polyvinylpolypyrrolidone crosslinked) and 221 g of sodium chloride are placed in a mixer cum granulation machine, e.g., Diosana®. This mixture Is mixed for 5 minutes and the solution of rivastigmine hta added to this slowly and wet-granulated. The wet mass is then passed through a 2 millimeters sieve and dried using a fluidised-bed drier at 60° C. After drying, the granules are passed through a sieve of 1 millimeter. The granules are weighed and mixed with the appropriate amounts of silica gel, e.g., Aerosil 200®, and microcrystalline cellulose for 20 minutes in a tumbling mixer (Turbula® mixer) and pressed as indicated above into cores each of 178 mg total weight. A 8 mm concave punch (R=12) in a tablet press having only one punch, e.g., Kilian EKO®, may be used.

B. Preparation of Film Lacquer 4000 compressed cores are coated with a semi-permeable film (or membrane) of the composition below using the fluidised bed process in a current of air, e.g., Glatt-wurster

| | |
|---|---|
| cellulose acetate containing 32% acetyl | 139.5 g |
| cellulose acetate containing 39.8% acetyl | 145.5 g |
| hydroxypropylmethyl cellulose (HPMC) | 15.0 g |
| methylene chloride | 6750 g |
| methanol | 750 g |

The film-coating (semi-permeable membrane coating) is effected with the above mentioned organic lacquer which contains 4% solid film constituent in a solvent mixture of methylene chloride methanol. However, other solvent mixture such acetone/alcohol/water instead of methylene chloride/methanol may also be used.

The cores are coated with layers of film of differing thicknesses, i.e., different weights, for example with approximately 55 mg, 70 mg, 80 mg/core, or more for obtaining lag-times of, e.g., 3–4, 5–6 or 7–8 hours, and dried in the current of air in a fluidised bed drier for 48 hours at 40°.

C. Compositions

| | Quantity/tablet (mg) |
|---|---|
| 1/Ingredients | |
| Polyplasdone-XL or Crosspovidone | 80.0 |
| Colloidal Silicone Dioxide | 5.0 |
| Sodium Chloride | 44.2 |
| Rivastigmine hta | 4.8 |
| Polyplasdone-XL or Crosspovidone | 20.0 |
| Avicel PH 102 | 23.0 |
| Magnesium Stearate | 1.0 |
| Core Weight | 178.0 |
| Cellulose Acetate E320 | 25.52 |
| Cellulose Aceate 398-10 | 26.74 |
| HPMC 603 | 2.74 |
| Total Weight | 233.0 |
| 2/Ingredients | |
| Polyplasdone-XL or Crosspovidone | 80.0 |
| Colloidal Silicone Dioxide | 5.0 |
| Sodium Chloride | 44.2 |
| Rivast[001b]igmine hta | 4.8 |
| Polyplasdone-XL or Crosspovidone | 20.0 |
| Avicel PH 102 | 23.0 |
| Magnesium Stearate | 1.0 |
| Core Weight | 178.0 |
| Cellulose Acetate E320 | 32.48 |
| Cellulose Aceate 398-10 | 34.03 |
| HPMC 603 | 3.49 |
| Total Weight | 248.0 |

D. Determination of the Release of Rivastigmine

Film-coated tablets as described above having two different film thicknesses (coated with a film of different weight) are placed in a beaker containing 200 ml of deionised (desalted) water of 37° C., and the time taken for the breaking of the film (semi-permeable membrane) of the two tablets is determined. The details are given in Tables 1 and 2:

TABLE 1 drug release DR (%) in water, 50 rpm. film thickness: 55 mg

| minutes | cell 1 | cell 2 | cell 3 | cell 4 | cell 5 | cell 6 |
|---|---|---|---|---|---|---|
| 0 | 0.0 | 0.0 | 0.0 | 0.0 | 0.0 | 0.0 |
| 120 | 0.8 | 0.7 | 0.9 | 0.9 | 0.7 | 0.7 |
| 150 | 0.7 | 0.8 | 0.7 | 0.7 | 0.6 | 0.7 |
| 180 | 0.7 | 0.8 | 0.7 | 0.7 | 0.6 | 0.7 |
| 210 | 53.4 | 1.4 | 0.9 | 0.7 | 46.9 | 0.6 |
| 240 | 64.0 | 64.4 | 67.0 | 0.7 | 57.5 | 0.7 |
| 300 | 76.6 | 81.7 | 89.5 | 69.8 | 69.7 | 82.1 |
| 360 | 83.1 | 92.2 | 94.5 | 77.7 | 78.4 | 86.8 |

TABLE 2 drug release DR (%) in water, 50 rpm, film thickness: 70 mg

| min | cell 1 | cell 2 | cell 3 | cell 4 | cell 5 | cell 6 |
|---|---|---|---|---|---|---|
| 0 | 0.0 | 0.0 | 0.0 | 0.0 | 0.0 | 0.0 |
| 240 | 0.6 | 0.4 | 0.3 | 0.3 | 0.3 | 0.2 |
| 270 | 0.5 | 1.0 | 1.3 | 0.8 | 0.5 | 0.6 |
| 300 | 45.6 | 0.3 | 42.9 | 46.8 | 0.5 | 2.2 |
| 330 | 63.7 | 59.1 | 61.8 | 61.0 | 33.0 | 45.1 |
| 360 | 72.7 | 71.2 | 69.8 | 70.1 | 51.2 | 56.0 |
| 420 | 84.7 | 84.0 | 81.6 | 81.8 | 65.7 | 69.5 |

EXAMPLE 5

Second Component in the Form of a Matrix Tablet Coated with Two Films

A. Preparation of the Core

The mass for 70,000 cores is prepared as follows. 336 g of rivastigmine hta is dissolved in about 6400 g of purified water and 12 g of alpha-tocopherol is dissolved in about 388 g ethanol (in case of BHT a similar solution would also be prepared). 6938 g of Polyplasdone-XL, 1660 g of Microcrystalline Cellulose, 3094 g of Sodium Chloride (previously milled), and 350 g of colloidal silicon dioxide (Aerosil 200) are sieved through a 1600 µm sieve and are transferred into a 75 L Collette Gral High Shear Mixer. In the Collette Gral the dry powders are mixed for one minute with Plow at slow speed and Chopper off. After that the alpha-tocopherol solution and the rivastigmine solutions are added slowly with the Plow and Chopper both operating at a slow speed. Additional purified water is added to form granules. After that the Collette Gral is operated for 2 minutes with the Plow at slow and Chopper at last speeds. Then the granules are dried in the fluidized bed dryer with inlet air temperature of about 70° C., till a Loss on Drying of less then 4% is achieved. After that the dried granules are sieved through an 800 µm sieve and mixed with the magnesium stearate (previously sieved) for 5 minutes in a free fall blender. This mixture is then compressed into tablets of 178 mg using oblong tooling of size 10×5.2 mm using a suitable tablet press.

B. Film Coating

First the two solutions for the two films are prepared. 499 g of Cellulose Acetate 398-10, 499 g of Cellulose Acetate 320S and 53 g of 3 cps HPMC are dissolved in a solvent mixture of 70% Acetone, 20% Ethanol and 10% Purified Water to form a 7.5% solution by weight of solid components. 441 g of Ethyl Cellulose N10 and 49 g of 5 cps HPMC are dissolved in a solvent mixture of 60% Acetone and 40% Ethanol to form a 5% solution by weight of the solid components. Up to 5% extra solution may be prepared to account for the loss from spray drying during the coating process. The tablets prepared above are coated in a suitable Perforated Coating Pan by spraying first the Cellulose Acetate solution and then the Ethyl Cellulose solution, to target film weights. Other solvent systems such as methylene chloride/methanol may also be used.

C. Compositions

| Ingredients | Quantity/tablet (mg) | |
|---|---|---|
| Rivastigmine hta | 4.8 | 4.8 |
| Sodium Chloride | 44.2 | 44.2 |
| Avicel PH 102 | 23.712 | 23.712 |
| PVPP-XL | 99.11 | 99.11 |
| a-tocopherol | 0.178 | 0.178 |
| Aerosil 200 | 5.0 | 5.0 |
| Magnesium Stearate | 1.0 | 1.0 |
| Core Weight | 178.0 | 178.0 |
| Cellulose Aceate 398-10 | 7.125 | 7.125 |
| Cellulose Acetate E320 | 7.125 | 7.125 |
| HPMC 603 | 0.750 | 0.750 |
| Ethylcellulose N10 | 4.5 | 6.3 |
| HPMC 5 cps | 0.5 | 0.7 |
| Total Weight | 198 | 200 |

In a further composition a-tocopherol may be replaced by BHT (butylated hydroxytoluene):

| Ingredients | Quantity/tablet (mg) |
|---|---|
| Rivastigmine hta | 4.8 |
| Sodium Chloride | 44.2 |
| Avicel PH 102 | 23.0 |
| PVPP-XL | 99.11 |
| BHT | 0.890 |
| Aerosil 200 | 5.0 |
| Magnesium Stearate | 1.0 |
| Core Weight | 178.0 |
| Cellulose Aceate 398-10 | 9.5 |
| Cellulose Acetate E320 | 9.5 |
| HPMC 603 | 1.0 |
| Ethylcellulose N10 | 2.7 |
| HPMC 5 cps | 0.3 |
| Total Weight (mg) | 201 |

D. Determination of the Release of Rivastigmine

TABLE 1 drug release DR (%) in water. 50 rpm, oblong tablet (approximate size 10.25 mm (millimeters) × 5.5 mm × 4.80–4.85 mm)

| minutes | cell 1 | cell 2 | cell 3 | cell 4 | cell 5 | cell 6 |
|---|---|---|---|---|---|---|
| 240 | 0.0 | 0.0 | 0.0 | 0.0 | 0.0 | 0.0 |
| 300 | 0.0 | 0.0 | 0.0 | 0.0 | 0.0 | 0.0 |
| 360 | 58.1 | 0.0 | 0.0 | 59.8 | 0.0 | 0.0 |
| 420 | 89.6 | 62.4 | 58.9 | 83.4 | 0.0 | 60.6 |
| 480 | 92.0 | 96.1 | 85.4 | 97.2 | 97.1 | 85.5 |
| 540 | 99.0 | 97.9 | 95.2 | 100.9 | 95.8 | 97.6 |
| 600 | 99.4 | 100.2 | 102.7 | 101.0 | 100.2 | 99.9 |
| 660 | 100.4 | 100.9 | 103.0 | 102.3 | 102.1 | 102.5 |
| 720 | 102.1 | 101.8 | 103.2 | 99.4 | 104.2 | 101.6 |

TABLE 2 drug release DR (%) in water. 50 rpm, round tablet (approximate size: 8.57 × 5.58 millimeters)

| minutes | cell 1 | cell 2 | cell 3 | cell 4 | cell 5 | cell 6 |
|---|---|---|---|---|---|---|
| 240 | 0.0 | 0.0 | 0.0 | 0.0 | 0.0 | 0.0 |
| 300 | 0.0 | 0.0 | 0.0 | 0.0 | 96.5 | 0.0 |
| 360 | 92.5 | 0.0 | 0.0 | 0.0 | 99.4 | 0.0 |
| 420 | 100.9 | 0.0 | 0.0 | 0.0 | 99.8 | 0.0 |
| 480 | 101.6 | 89.5 | 0.0 | 0.0 | 100.3 | 0.0 |
| 540 | 101.5 | 98.0 | 0.0 | 0.0 | 100.2 | 88.7 |
| 600 | 100.9 | 100.1 | 94.4 | 0.0 | 99.4 | 97.0 |
| 660 | 101.7 | 101.7 | 100.1 | 0.0 | 98.8 | 101.0 |
| 720 | 102.1 | 100.7 | 101.8 | 76.2 | 99.2 | 102.1 |

EXAMPLE 5

Capsule Filing

The capsule filling mixture comprising first and second component together (or alone it desired) is filled on a automatic capsule filling machine (Zanasi® LZ 5) into empty hardgelatine capsule shells (CONISNAP® 6 dimple, size 3). The nominal fill weight is as mentioned above. The process parameters are as follows:

speed: 3000 HK/h
dosator/piston:
  size: # 4
  height: 12–14 mm
vacuum: 0.7 bar
feed hopper: none

What is claimed is:

1. A pharmaceutical composition comprising Rivastigmine having the following release characteristics in water:

| time (minutes) | amount (percentage) |
|---|---|
| 30 | 1–40 |
| 60 | 10–60 |
| 120 | 40–80 |
| 180 | 60–90 |
| 240 | 65–95 |
| 300 | 70–99 |
| 360 | 75–99 |
| 420 | >80. |

2. A controlled release, oral pharmaceutical composition containing rivastigmine having the following release characteristic in water or artificial stomach juices:

| time (minutes) | amount (percentage) |
|---|---|
| 30 | 1–8 |
| 60 | 15–25 |
| 120 | 45–70 |
| 180 | 75–90 |
| 240 | 92–95 |
| 300 | 95–98 |
| 360 | 97–99 |
| 420 | >99. |

3. A controlled release, oral pharmaceutical composition containing rivastigmine having the following characteristic in water or artificial stomach juices:

| time (minutes) | amount (percentage) |
| --- | --- |
| 30 | 5–25 |
| 60 | 25–45 |
| 120 | 50–70 |
| 180 | 65–80 |
| 240 | 70–90 |
| 300 | 75–95 |
| 360 | 80–90 |
| 420 | 85–95 |
| 480 | 85–95. |

4. A controlled release, oral pharmaceutical composition containing rivastigmine having the following release characteristic in water or artificial stomach juices:

| time (minutes) | amount (percentage) |
| --- | --- |
| 30 | 25–40 |
| 60 | 45–65 |
| 120 | 65–85 |
| 180 | 75–95 |
| 240 | 75–96 |
| 300 | 85–97 |
| 360 | 87–98 |
| 420 | 90–98 |
| 480 | 90–99. |

5. A pharmaceutical oral controlled release tablet composition comprising rivastigmine having the following release characteristic in water or artificial stomach juices:

| time (minutes) | amount (percentage) |
| --- | --- |
| 30 | 28–35 |
| 60 | 40–55 |
| 120 | 58–75 |
| 180 | 70–90 |
| 240 | 80–95 |
| 300 | 88–98 |
| 360 | >92. |

6. A pharmaceutical oral controlled release tablet composition comprising rivastigmine wherein in use 60 to 90% of said rivastigmine is released in artificial stomach juices within 3 hours.

* * * * *

UNITED STATES PATENT AND TRADEMARK OFFICE
CERTIFICATE OF CORRECTION

PATENT NO.    : 6,565,883 B2
DATED         : May 20, 2003
INVENTOR(S)   : Ogorka et al.

It is certified that error appears in the above-identified patent and that said Letters Patent is hereby corrected as shown below:

Title page,
Item [*] Notice, delete the phrase "by 0 days" and insert -- by 17 days --
Item [56], References Cited, U.S. PATENT DOCUMENTS, the last referenece should read:
-- 6,110,494    8/2000 Clancy et al.    424/461 --

Signed and Sealed this

Thirtieth Day of March, 2004

JON W. DUDAS
*Acting Director of the United States Patent and Trademark Office*